United States Patent [19]
Häussinger

[11] Patent Number: 5,880,098
[45] Date of Patent: Mar. 9, 1999

[54] THERAPEUTIC TREATMENT

[75] Inventor: Dieter Häussinger, Düsseldorf, Germany

[73] Assignee: Pharmacia & Upjohn Aktiebolag, Stockholm, Sweden

[21] Appl. No.: 878,557

[22] Filed: Jun. 19, 1997

Related U.S. Application Data

[60] Provisional application No. 60/016,112 Jun. 19, 1996.

[30]     Foreign Application Priority Data

Apr. 12, 1996 [SE] Sweden ................................. 9601396
Apr. 12, 1997 [WO] WIPO ..................... PCT/EP97/01861

[51] Int. Cl.$^6$ ...................... A61K 31/70; A61K 31/685; A61K 31/205; A61K 31/185
[52] U.S. Cl. .............................. 514/23; 514/77; 514/556; 514/578; 514/738
[58] Field of Search ............................ 514/23, 77, 556, 514/578, 738

[56]                    References Cited

U.S. PATENT DOCUMENTS 5,342,832    8/1994   Siren ....................................... 514/103

FOREIGN PATENT DOCUMENTS

| 0 359 257 A2 | 3/1990 | European Pat. Off. |
| 43 31 711 A1 | 3/1994 | Germany . |
| 43 16 293 A1 | 11/1994 | Germany . |
| 3-81219 | 4/1991 | Japan . |
| WO 91/09601 | 7/1991 | WIPO . |
| WO 91/14435 | 10/1991 | WIPO . |
| WO 92/15546 | 9/1992 | WIPO . |
| WO 95/34301 | 12/1995 | WIPO . |
| WO 96/32906 | 10/1996 | WIPO . |

OTHER PUBLICATIONS

Raschke et al., Free Radical Biol. Med. (1995), 19(4), 461–71 (Abstract), 1995.

Rao et al, *Ann. Thorac. Surg.*, vol. 52, No. 4, 1991, pp. 908–912.

Minor et al, *Adv. Exp. Med. Biol.*, vol. 403, 1996, pp. 157–161.

Wingenfild et al, *Adv. Exp. Med. Biol.*, vol. 359, 1994, pp. 159–169.

Canas, *Acta Physiol. Pharamcol. Ther. Latinoam.*, vol. 42, No. 3, 1992, pp. 133–137.

Decker, K. Biologically active products of stimulated liver macrophages (Kupffer cells), *Eur. J. Biochem.* 192, 245–261 (1990).

Kajstura, J., et al. Apoptotic and Necrotic Myocite Cell Deaths are Indepedent Contributing Variables of Infarct Size in Rats, *Laboratory Investigation*, 74, 86–107 (Jan. 1996).

Petronini, P.G., et al. Modulation by betaine of cellular responses to osmotic stress, *Biochem J.*, 282, 69–73 (1992).

Warskulat, U., et al. Betaine is an osmolyte in RAW 264.7 mouse macrophages, *FEBS Letters*, 377, 47–50 (1995).

Weissberg, P.L., Is vascular smooth muscle cell proliferation benefical?, *Lancet*, 347, 305–07 (1996).

Zhang, F., et al. Hyperosmolarity stimulates prostaglandin synthesis and cyclooxygenase–2 expression in activated rat liver macrophages, *Biochem. J.*, 312, 135–143 (1995).

*Primary Examiner*—Phyllis G. Spivack
*Attorney, Agent, or Firm*—Pollock, Vande Sande & Amernick

[57]                    ABSTRACT

The present invention is directed to a therapy involving administering effective amounts of an organic osmolyte selected from the group consisting of polyols, amino acids and methyl amines, that regulate hydration of certain cells, for treating or preventing complications resulting from ischemia, hypoxia or oxidative stress.

13 Claims, 8 Drawing Sheets

THERAPEUTIC TREATMENT

This application is a continuation-in-part of provisional application Ser. No. 60/016,112, filed Jun. 19, 1996.

FIELD OF INVENTION

The present invention relates to the use of organic osmolytes in the manufacture of a therapeutic agent capable of treating or preventing complications resulting from ischemia, hypoxia or oxidative stress.

BACKGROUND OF THE INVENTION

In recent studies it has been revealed that, immune competent cells with macrophage activity such as the Kupffer cells have a remarkably sensitive and potent osmoregulation, see e.g. Biochem J. 1995, Vol. 312, pag. 135–142, F Zhang et al. The studies suggest that cell volume homeostasis is a critical factor for the cellular function of Kupffer cells. This type of organic osmolytes need to be non-perturbing solutes that do not interfere with protein function even when occurring at high intracellular concentrations. Such a prerequisite may explain why only a few classes of organic compounds, viz. polyols (e.g. inositol and sorbitol), methylamines (betaine, α-glycerophosphorylcholine) and certain amino acids such as taurine have evolved as osmolytes in living cells. In mammals, osmolytes have been identified in astrocytes, renal medulla cells and lens epithelia. The need for osmolytes in renal medulla cells is obvious, because ambient medullary osmolarity can increase up to 3800 mosmol/l during antidiuresis and decrease to 170 mosmol/l during diuresis. In the antidiuretic state (high extracellular osmolarity), intracellular osmolarity increases in renal medullary cells as the result of the intracellular accumulation of inositol and betaine which are taken up via sodium ion dependent transporters. These sodium ion dependent transporters are induced upon hyperosmotic exposure in renal cells and astrocytes. Recent studies with Madine-Darby canine kidney (MDCK) cells have identified a hypertonic stress-responsive element in the 5'-flanking region of the mammalian BGT-1 gene (betaine transporter).

In a study disclosed in FEBS Letters, 1995, Vol. 377, pages 47–50, U Warskulat et al., betaine is identified as osmolyte in mouse macrophages. The betaine uptake in mouse macrophages was significantly stimulated when the cells were exposed to a hyperosmotic (405 mosm/l) medium. From the results of this study it was concluded that betaine availability could be a potential site for the regulation of macrophage cell function.

Certain organic osmolytes have previously been suggested in the International Patent Application WO 91/14435 as supplements to protect cells in a dehydrated environment from volume changes. Also in Biocbem. Journal, 1992, Vol. 282, pages 69–73, it is demonstrated that SV-3T3 cells (fibroblasts) subjected to hyperosmotic conditions may retain normal function in terms of rate of cell proliferation and protein synthesis in the presence of an osmolyte. Even if these publications may consider a therapeutic utility of certain osmolytes, there are no disclosures of how osmolytes can affect cells which mediates pathological events resulting from ischemia, hypoxia or oxidative stress, both during hyperosmolar conditions and in conditions with normal osmolarity.

Organ transplantation has become an established therapy for end stage liver and heart disease, although primary graft non-function or dysfunction is serious clinical problem. Cold ischemic storage and the following reperfusion of the donated organ are identified as major contributors to failing primary graft function and is shown to have a detrimental impact on endothelial and immune competent cells, injuries to the endothelial cells precipitates a malfunction vascular system and consequently, an inadequate oxygen and substrate delivery, as well as an impaired waste product clearance. Furthermore, the challenged endothelium enhances the expression of adhesive molecules facilitating the binding and infiltration of immune competent cells in the tissue area at risk. Immune competent cells respond to ischemia and reperfusion by producing a number of biologically toxic mediators, again leading to the dysfunction of surrounding cells, including the vascular endothelium and in certain cases the whole organ. The early organ dysfunction is considered to originate from injuries of endothelial cells resulting in inadequate oxygen and substrate delivery as well as reduced waste product clearance. Beyond transplantation injuries, resulting from ischemia and reperfusion, these are a well recognized clinical problems in, for example, myocardial infarction and the following thrombolytic treatment. As disclosed in Laboratory Investigation, 1996, Vol. 74, No. 1, p. 86 (J Kajstura et al.), both myocardial ischemia and hypoxia can induce cell death, such as programmed cell death (apoptosis) in the heart following myocardial infarction which may lead to massive loss of cells and further organ damages.

In the liver, the inflammatory response to ischemia and reperfusion is suggested to be primarily mediated by resident macrophages, the Kupffer cells, while the heart in such a situation suffers from invading immune competent cells which might cause persistent injuries.

It would consequently be highly desirable to find a suitable therapy to preserve or improve the endothelial cell function and diminish the inflammatory response of the immune competent cells during and after the mentioned complications, as well as form a protection against cell death.

In response to ischemia/reperfusion and inflammatory mediators, endothelial and immune competent cells produce oxygen free radicals which exert a detrimental metabolic load on exposed cells termed oxidative stress. The oxidative stress precipitates severe damages to biological molecules, especially to DNA, lipids and proteins. The protection against oxidative stress and hence the salvage of tissues and organs might be achieved only partially by supplying anti-oxidants and ensuring an adequate level of antioxidant enzymes. It would therefore also be desirable to be able to provide a therapy which also is useful for improving the protection of cells against damages originating from oxidative stress.

In the International patent application WO 92/15546 certain osmolytes, such as taurine, which are capable of crossing the blood brain barrier, are suggested in the protection of cells being at risk to be damaged from lactic acidosis from oxygen deficiency. In this publication, however, the osmolyte exert its beneficial effect by providing buffering action and not by directly acting on specific cells in order to modulate their response to the disorderly event. Furthermore, the osmolyte taurine has been suggested to have certain beneficial effects to heart in Japanese Circ. Journ. 1992, Vol. 56, p. 95 (J Azuma et al.) following congestive heart failure. It is concluded that taurine possibly contributes to a regulation of the myocardial calcium uptake and thus may increase the myocardial activity. According to the present invention, it has been surprisingly found that certain osmolytes, such as betaine and taurine, have a powerful capacity to maintain the cellular integrity in specific cells, and thereby the organ function, subjected to a depletion of oxygen in an anoxia model or oxidative stress, as demonstrated in an isolated, perfused liver. The present invention shows that selected osmolytes can be employed as important regulators of endothelial and immune competent cell function. The osmolytes have a capacity to protect these cell types or to affect such cells to modulate their response to the mentioned complications and thereby maintaining the function of vital organs challenged by pathologic events, such as an inadequate blood supply.

The failing liver is an early event in sepsis and accompanied by raised enzyme leakage from the liver, for example lactate dehydrogenase (LDH) which indicates a compromised cellular integrity. As a sign of an adequate treatment, the hepatic function and enzyme leakage is restored to near normal levels within days. This course of pathological events and the impact of a successful treatment, reflects the clinical importance of the marked decrease in LDH leakage in response to osmolyte treatment following anoxia, as will be described in the present invention.

Consequently, it is an object of the present invention to preserve and improve the endothelial cell function and diminish the inflammatory response of the immune competent cells by a supplementation of an effective amount of certain osmolytic agents. It is also an object of the present invention to, by means of an osmolyte therapy, to improve the capacity of the tissue to resist oxidative stress, in order to prevent and treat damages resulting from such a condition and thereby improve the possibility of organ protection and rescue.

The present invention demonstrates that otherwise metabolically inert osmolytes have a high potency in protecting organs or tissues from such damages and dysfunctions resulting from ischemia and reperfusion, hypoxia or oxidative stress.

DESCRIPTION OF THE INVENTION

The present invention is related to the use of an effective amount of an osmolyte in the preparation of a therapeutic agent capable treating or preventing complications resulting from ischemia, hypoxia or oxidative stress by affecting cells which produce mediators of such complications. Such cells may have an active part in the immune system and typically include, but are not strictly limited to, immune competent cells, endothelial cells and hepatocytes. In particular, this type of cells are protected to maintain their regular metabolic function or are affected to modulate their response to the complications of ischemia, hypoxia and oxidative stress, in order to maintaining the function of vital organs challenged from pathologic events, such an inadequate blood supply. These complications typically can involve phenomena as cell death exemplified by programmed cell death (apoptosis) and necrosis, as well as an increase in the activity of inducible nitric oxide synthase (iNOS). The ischemic or hypoxic conditions typically origin from a situation where the ordinary blood flow of substrates to an organ or a tissue is interrupted or reduced, so the regular metabolism is altered. Such situations can occur in connection to a large variety of traumatic events, such as myocardial infarction, bypass surgery of the heart or other organs or organ transplantation.

It is also an important aspect of the present invention to use effective amounts osmolytes in the manufacture of a preparation that is capable of preventing complications which can arrive from ischemia, hypoxia or oxidative stress for patients who are identified to be at high risk for acquiring such a complication. The present invention also serves as a cytoprotective therapy by increasing a correct cellular hydration in response to stress. In particular patients suffering from identified vascular dysfunctions, such as those suffering from the effects or diabetes or who are expecting additional surgery or therapy can benefit from a therapy with selected osmolytes according to the present invention in connection with their regular therapy.

The osmolytes are defined as agents used by the cells to regulate the level of hydration by a specific transport mechanism through the cellular membranes. Such agents traditionally have been considered biologically inert, except for their function as substrates in metabolic pathways. In the context of the present invention, the osmolytes are defined as agents that are used in the regulation of the cellular hydration with the additional capacity to protect organs against injuries resulting from ischemia, hypoxia and oxidative stress. In addition, such osmolytes are useful for the preservation of the organ function at abnormal temperatures (hypothermia) induced during preservation prior to the transplantation. The osmolytes are preferably selected from a group consisting of polyols, amino acids and methylamines which are endogenously occurring in the body for regulating the individual cellular volume and osmolarity after exposure to osmotic variations and other stimuli related to the immune defense, as explained in our co-pending Swedish patent application 9601395-8.

According to the present invention, it is especially preferred to use amino acid osmolytes, methylamine osmolytes, such as taurine and betaine and certain polyols, such as myo-inositol, but the skilled person could be able to identify other individual osmolytes capable of acting as an osmolarity regulating agent for specific cells of an elected organ or of a certain tissue and such compounds will also be conceivable to use within the context of the present invention. The osmolytes can be administered as salts or as precursors, such as alkyl esters of osmolytes or osmolytes in oligopeptides, capable of being released at their functional cellular target. All such administration forms especially selected for delivering the osmolyte to the cells, therefore are parts of the present invention. Alternatively, biological precursors to osmolytes can be administered when suitable, as is examplified by a supplement of choline as a precursor to betaine. As an example, choline can be converted to betaine by hepatocytes for transport to the Kupffer cells of the liver where it may exert the mentioned effects. Choline can however not be converted to betaine by the Kupffer cells.

According to the present invention it is possible to add one or several constituents capable of contributing to a prevention of the impairing effects resulting from the ischemic or hypoxic conditions. Examples of such compounds are for example, found among certain amino acids, their precursors and derivatives, such as alpha-ketoglutarate as disclosed in WO 95/34301 (Pharmacia AB) which hereby is incorporated as a reference.

An important aspect of the present invention is to use therapeutically effective amounts of an osmolyte and a thrombolytic agent in combination for the manufacture of an agent capable of treating complications resulting from ischemia, hypoxia or oxidative stress. Such an agent will be especially useful for treating complications in relation to myocardial infarction wherein the thrombolytic agent with a capacity to induce lysis of blood clots, or the procedure of percutaneous transluminal coronary angioplasty (PTCA) is combined with osmolytes to minimize the risk of coronary and vascular damages and restenosis. It is the intention that conventionally employed agents with thrombolytic activity such as streptokinase shall be used in combination with osmolytes of the types described above.

The present invention is also related to a composition comprising an effective amount of the mentioned osmolytes for administration to an organ or a tissue being subjected, or at the risk of being subjected, to an insufficient supply of substrates necessary for maintaining the normal metabolic function together with a pharmacologically acceptable carrier. Such compositions are especially suitable for being supplied to the heart in connection with its interruption from a regular blood flow for example for treating myocardial infarction, during coronary bypass surgery or transplantation. Such compositions can further comprise agents as incorporated in conventional preservation solutions or cardioplegic agents, such as Plegisol® (Abbott Laboratories), St. Thomas solution or the University of Wisconsin solution or other preservative agents or energy substrates as suggested in WO 95/34301.

For the treatment of myocardial infarction, the compositions can preferably as mentioned be combined with a conventional thrombolytic agent, such as streptokinase. The thrombolytic agent can be added to the osmolytic composition, or administered separately in a predetermined manner. The inventive compositions can also be included in blood cardioplegia and in solutions useful as blood substitutes.

The compositions according to the present invention are also useful as solutions for the preservation of organs interrupted from their regular blood flow in combination with conventional preservative agents.

It is also a part of the present invention to provide compositions for the treatment of patients suffering from diabetes or such post-traumatic patients dependent on an insulin therapy, comprising an effective amount insulin in a conventional dosage form together with a therapeutically effective amount of at least one of the selected osmolytes, as mentioned above. Such a composition can be in the form of an injectable preparation or an otherwise administerable dosage form of a conventional insulin in an effective amount, either directly mixed with osmolytes, or with the osmolyte preparation separately administerable in the as a part of kit, to be self administered by the patient in the connection with the insulin therapy.

Effective amounts of the osmolytes in the inventive compositions shall, suitably after administration, provide between about 50 $\mu$M up to about 10 mM of osmolyte concentration in the fluid supplied to the organ or the tissue, preferably between a concentration of about 0.1 mM up to about 1–2 mM and most preferably about 0.5 mM. An especially effective composition has been shown to comprise betaine and taurine at a total concentration of about 0.2 mM.

DETAILED AND EXEMPLIFYING DESCRIPTION OF THE INVENTION

FIG. 1 shows an anoxic model on a perfused liver, wherein lactate dehydrogenase (LDH) in the effluent is used as a marker on cellular impairments is plotted against the perfusion time for control and the incorporation of 0.1 mM and 1 mM of betaine in the perfusion solution of 385 mosm/l, respectively.

FIG. 2 shows the effect of ambient osmolality on mRNA levels for the betaine transporter (BGT-1), the taurine transporter (TAUT), the myo-inositol transporter (SMIT) and GAPDH in the rat liver endothelial cells. Changes in osmolality were performed by appropriate addition/removal of sodium chloride. The mRNA levels were determined by Northern blot analysis.

FIG. 3 shows the time-dependent induction of BGT-1 (betaine transporting protein) and TAUT (taurine transporting protein) and SMIT (the myo-inositol transporter) mRNA-levels in rat Kupffer cells. The Kupffer cells were exposed to LPS (1 $\mu$g/ml) in normoosmotic (305 mosmol/l) or hyperosmotic (405 mosmol/l) media for the time periods indicated and mRNA levels for BGT-1, TAUT, SMIT and glyceraldehydephosphate dehydrogenase (GAPDH) as a standard were determined by Northern blot analysis.

Figure 7A:
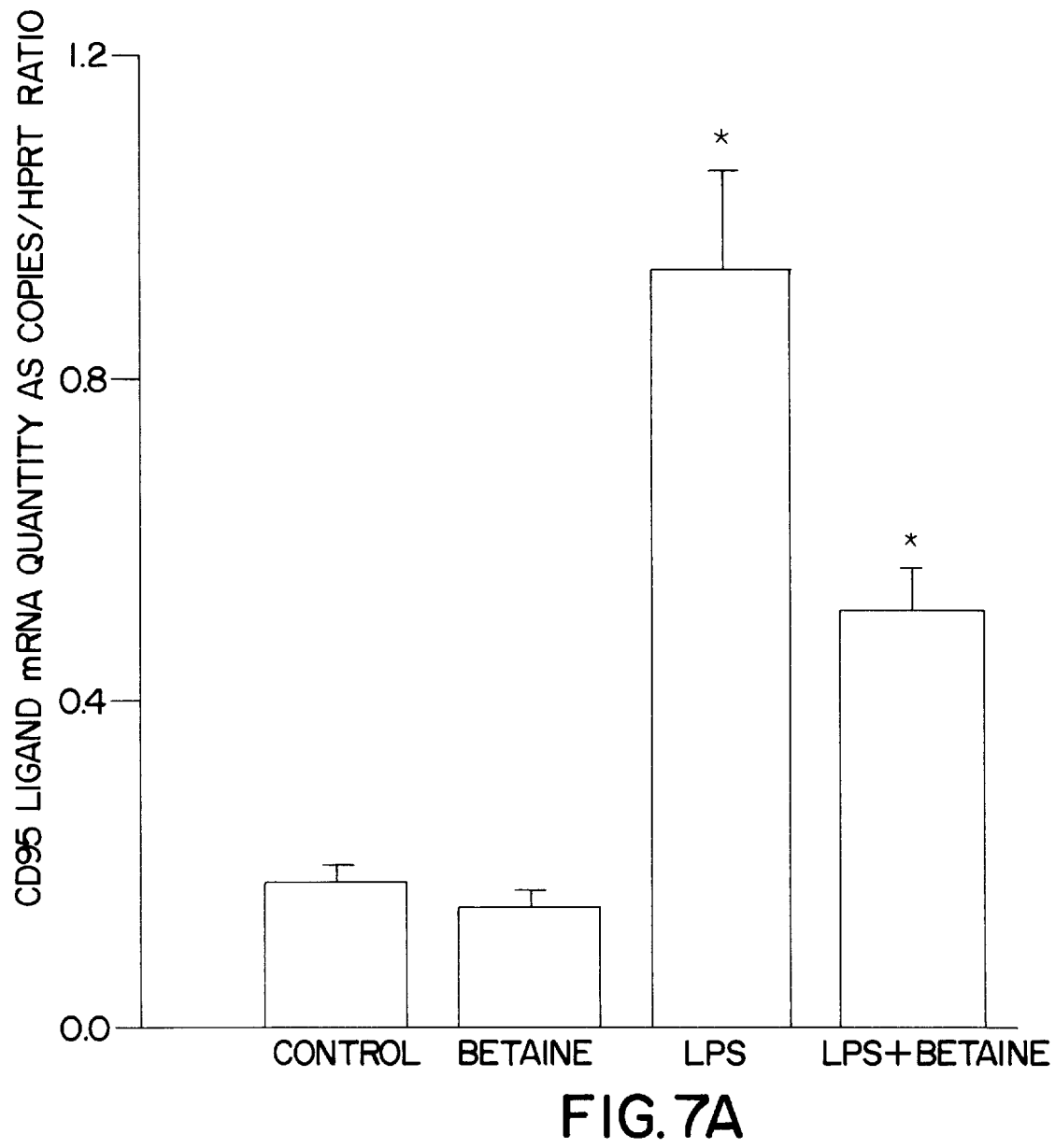

FIG. 7A shows the modulation of the CD95 ligand mRNA expression (a mediator for apoptosis) in rat Kupffer cells in response to LPS challenge (1 ug/ml for 6 h). In experiments shown in bars 1 and 2, the cells were not incubated with LPS. In experiments shown in bars 2 and 4, 5 mmol/l betaine was added 30 min before and throughout the whole 6 h measurement period. Total RNA was extracted, reverse transcribed and quantified by using PCR technique. Results are expressed as the ratio of number of CD95 ligand transcripts obtained with the indicated primers to the numbers of rat hypoxanthine-guanine phsophoribyltransferase (HPRT) transcripts.

Figure 7B:
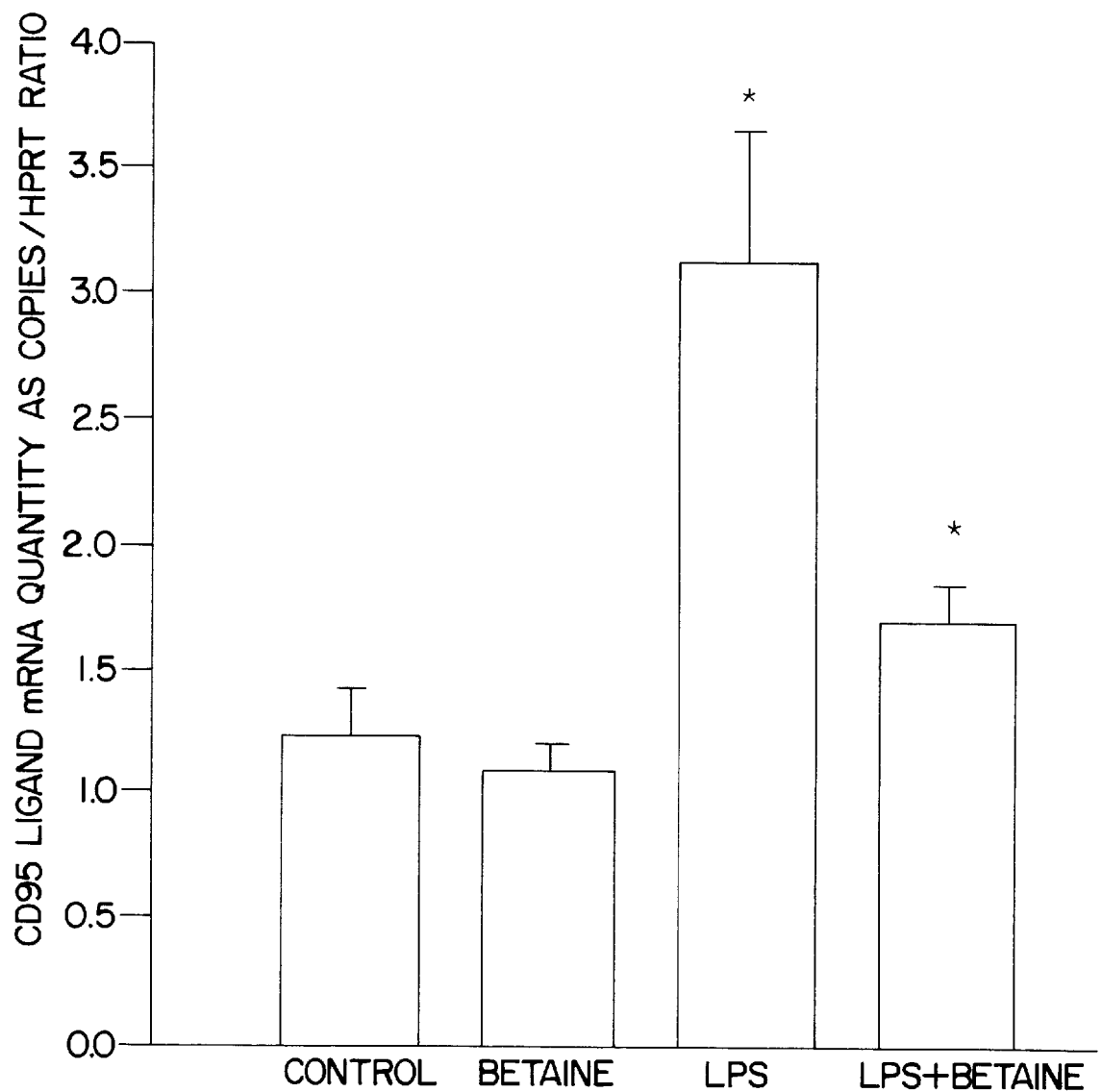

FIG. 7B shows the same experiment as in FIG. 7A performed with rat sinusoidal endothelial cells.

Figure 8:
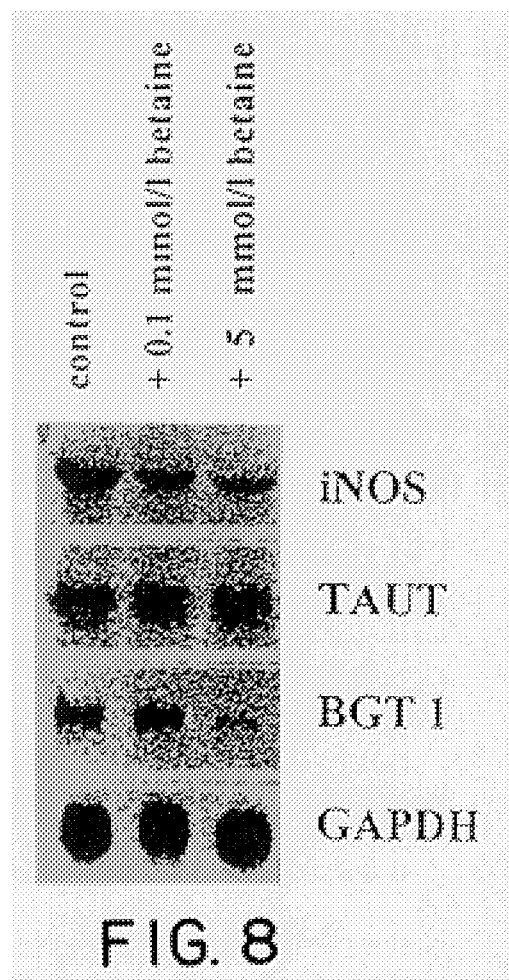

FIG. 8 shows the influence of betaine on the transporters for betaine and taurine (BGT-1 and TAUT) and on inducible nitric oxide synthase mRNA levels in RAW 264.7 mouse macrophages during hyperosmolarity. The macrophages were exposed to LPS (1 $\mu$g/ml) for 6 hours in the presence or absence of 0.1 or 5 mmol/l betaine. The mRNA levels of the transporters and iNOS were determined by Northern blot analysis.

MATERIAL AND METHODS

Isolation and culture of Kupffer cells

Kupffer cells from male Wistar rats of 300–400 g body weight raised in the local institute for laboratory animals were isolated by collagenase-pronase perfusion and separated by a single Nycodenz gradient and centrifugal elutriation. Cells were cultured in RPMI 1640 medium supplemented with 10% heat-inactivated fetal calf serum (FCS) for 48 h. The experiments were performed during the following 24 h using Krebs-Henseleit hydrogen carbonate buffer (pH 7.4) containing 10 mM glucose and 1% FCS. At that time the cultures consisted of more than 99% Kupffer cells as demonstrated by their morphological appearance and their ability to phagocytose 1 $\mu$m Latex particles, which is not observed in cultured endothelial cells. The osmolarity was varied by changing the NaCl concentration. The viability of Kupffer cells was more than 95% as assessed by trypan blue exclusion. Kupffer cell volume was measured by flow resistance cytometry using a Casy 1 cell counter and analyzer system (Scharfe Systeme, Reutlingen, Germany). In normoosmotic medium, the average Kupffer cell volume was 724±24 fl (7 different preparations). Protein content was 0.039±0.009 mg per 106 cells (n=7). Assuming a water content of 80% of whole Kupffer cell volume, a mean intracellular water space of 14,9 µl/mg protein is estimated. Viability of the incubations was routinely tested by lactate dehydrogenase (LDH) release at the end of the incubation. 12–24 h hyperosmotic (405 mosmol/l) or a hypoosmotic (205 mosmol/l) exposure was without effect on LDH release. Culture medium RPMI 1640 (without phenol red) and fetal calf serum (FCS) were from Biochrom (Berlin, Germany)

Isolation and culture of endothelial cells

Endothelial cells of male Wistar rats were isolated according to the collagenase-pronase method and centrifugal elutriation technique, as described for the Kupffer cells. Isolated endothelial cells were incubated the first day for 4 hours in the appropriate culture medium adjusted to the desired osmolarity (205, 255, 305 or 405 mosmol/l). The cells were harvested following incubation and used for mRNA analysis. The cell viability was routinely tested by determination of enzyme leakage, 4 hours of a hyperosmotic (405 mosml/l) or a hypoosmotic incubation was without effect on viability.

Liver perfusion

Livers of Wistar rats (100–150 gram body mass) were perfused in situ as described in Eur. J. Biochem., 1989, Vol. 181, p. 709–716, in the physiological antegrade direction (from portal to hepatic vein) in an open recirculating system. The perfusion medium used was bicarbonate buffered Krebs-Henseleit saline medium (equlibrated with $O_2/CO_2$ 95:5 by volume). Anoxia was introduced by interrupting the supply oxygenated buffer Cell and organ integrity was measured as release of lactate dehydrogenase (LDH) in the liver effluent. The determination of the LDH content was performed according to a routine spectrophotometric technique and expressed as milliunits/gram liver and minute.

Northern blot analysis

Total RNA from near-confluent culture plates of Kupffer cells and endothelial cells were isolated by using guanidinethiocyanate solution. RNA samples were electrophoresed in a 0.8% agarose/3% formaldehyde and then blotted onto Hybond-N nylon membranes with 20× SSC (3M NaCl, 0.3M sodium citrate). After brief rinsing with water and UV-crosslinking (Hoefer UV-crosslinker 500), the membranes were inspected under UV illumination to determine RNA integrity and location of the 28S and 18S rRNA bands. Blots were then subjected to a 3 h-prehybridization at 43° C. in 50% deionized formamide, in sodium phosphate buffer (0.25M, pH 7.2), containing 0.25M NaCl, 1 mM EDTA, 100 mg/ml salmon sperm DNA and 7% SDS. Hybridization was carried out in the same solution with approx. 106 cpm/ml ($\alpha$-32P)dCTP-labeled random primed BGT-1, TAUT and GAPDH cDNA probes. Membranes were washed three times in 2× SSC/0.1% SDS and twice in sodium phosphate buffer (25 mM, pH 7.2)/EDTA (1 mM)/1% SDS. Blots were then exposed to Kodak AR X-omat film at 70° C. with intensifying screens and analysed with PDI densitometry scanning (Pharmacia, Freiburg, Germany).

Statistics

Values are expresses as mean S.E.M (n=number of preparations).

Discussion of the results

Figure 1:
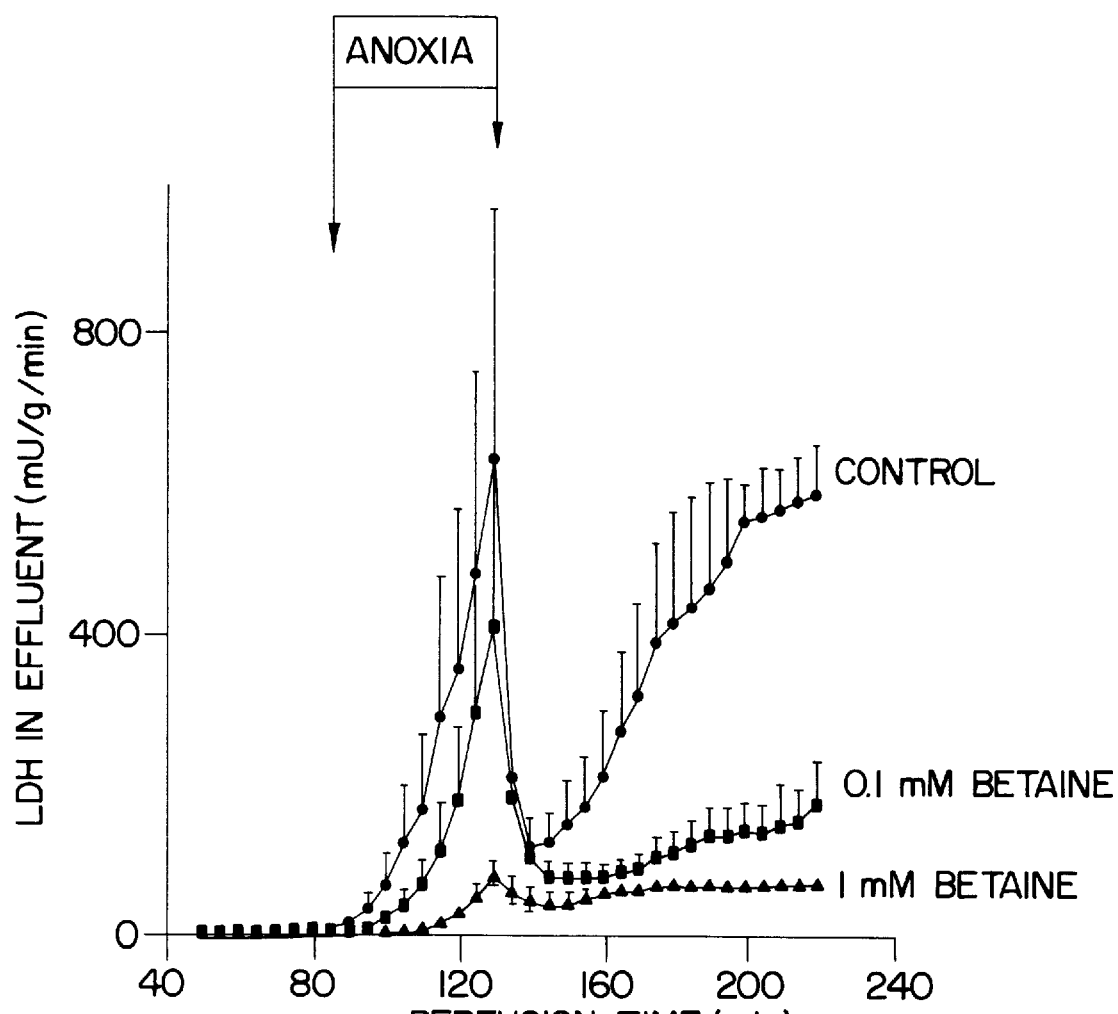

As shown in FIG. 1, hypoxia resulted in a marked increase in LDH release demonstrating a deteriorating cell and organ integrity and function. The described cell and tissue damage was characterized by an early injury, evident during hypoxia challenge recognized by an escalating LDH release and a late injury when normoxia was reinstituted (reperfusion injury). In a dose dependent manner, treatment with 0.1 mM and 1 mM betaine solution was determined to diminish or even abolish the injury during and following hypoxia.

Figure 2:
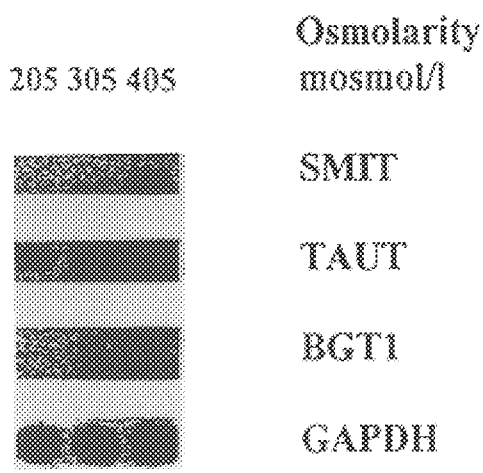
Figure 3:
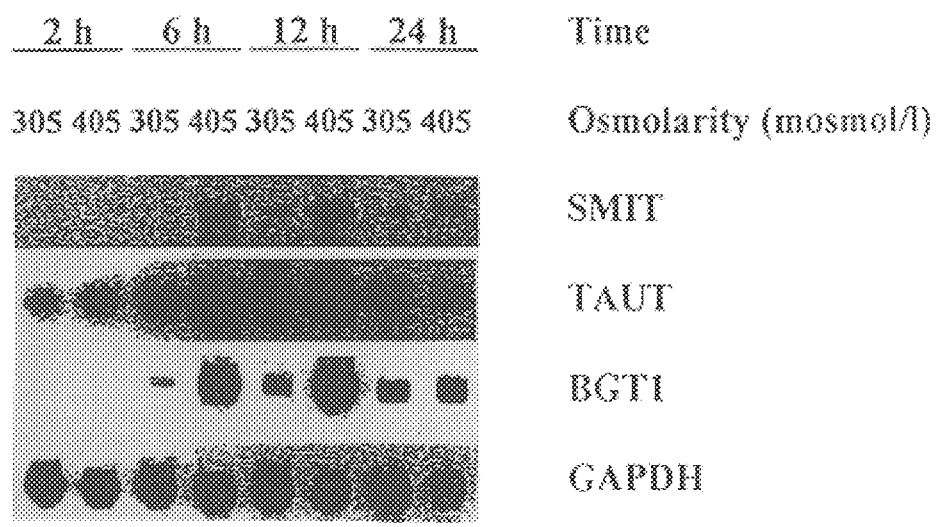

FIG. 2 and FIG. 3 show that mRNA for the betaine transport protein, BGT-1, the taurine transport protein, TAUT and the myo-inositol transporter SMIT, were expressed both in endothelial cells and Kupffer cells. The endothelial cells were strongly dependent on ambient osmolarity (FIG. 2) which demonstrates that osmolytes are important components in the regulation of cellular function in both immune competent cells and the endothelial cells of the vasculature. Moreover, in endothelial cells TAUT tended to be more intensively expressed than BGT-1 in response to the 4 hours of exposure to hyperosmolarity. In Kupffer cells, there was a time dependent increase in BGT-1 and TAUT mRNA expression, see FIG. 3. These findings shows that the composition of osmolytes, used according to the present invention, can be tailored to optimize therapeutic efficacy with respect to a target cell type, as well as the timing of the therapeutic intervention.

Figure 4:
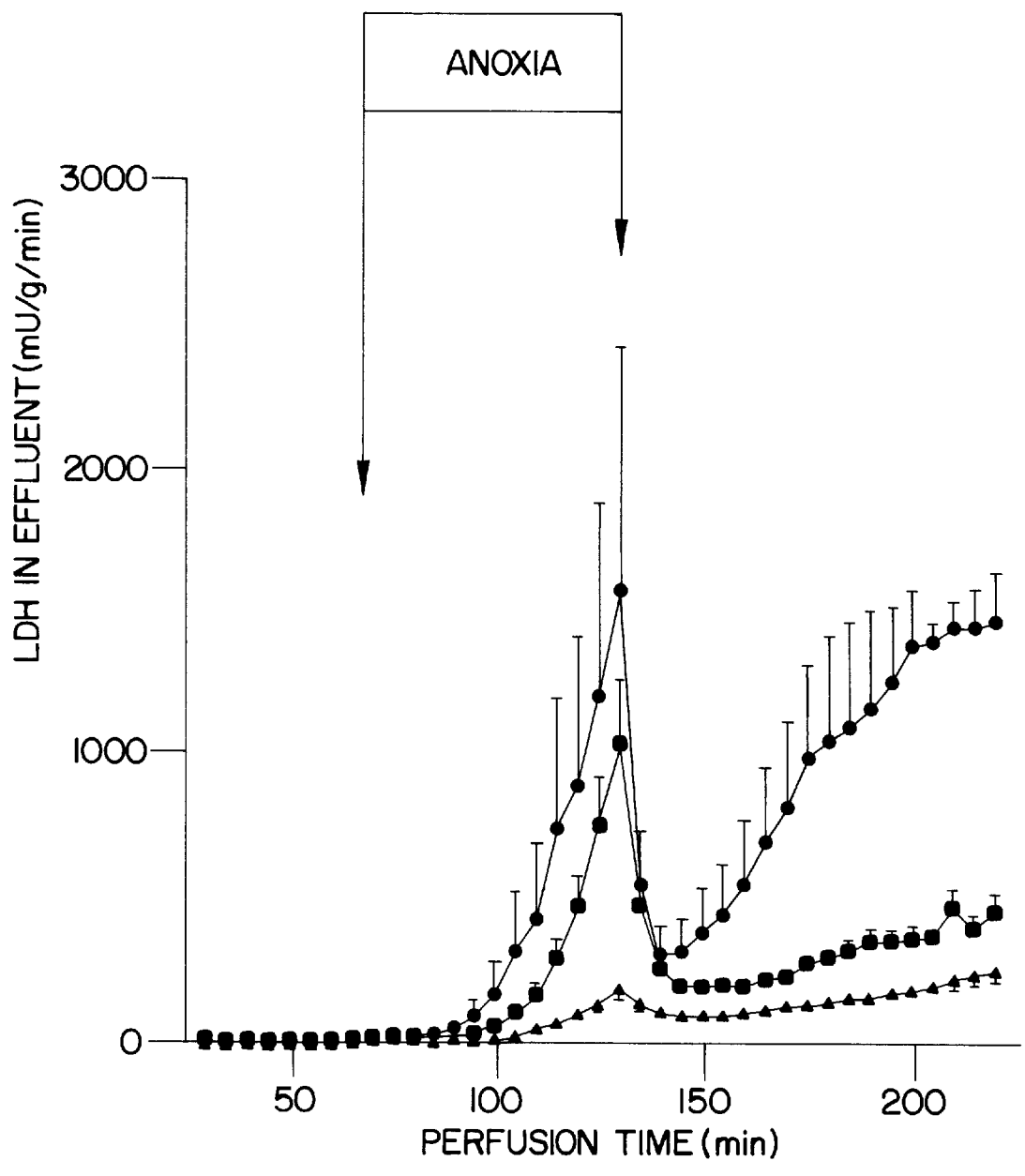
FIG. 4 shows an anoxic model on perfused liver similar to the one shown in FIG. 1, wherein the LDH release is measured in the effluent after perfusion with solutions of 385 mosmM enriched with 0.100 mM betaine, 0.100 mM betaine+0.100 mM taurine.

FIG. 4 shows that a co-administration of taurine and betaine during anoxia leads to a reduced leakage of LDH from the Kupffer cells, when compared to a supplementation of betaine only, or a standard solution of 385 mosmM. These results demonstrates a possibility of obtaining an improved, or even a synergistic, organ protection by combining different selected osmolytes.

Figure 5:
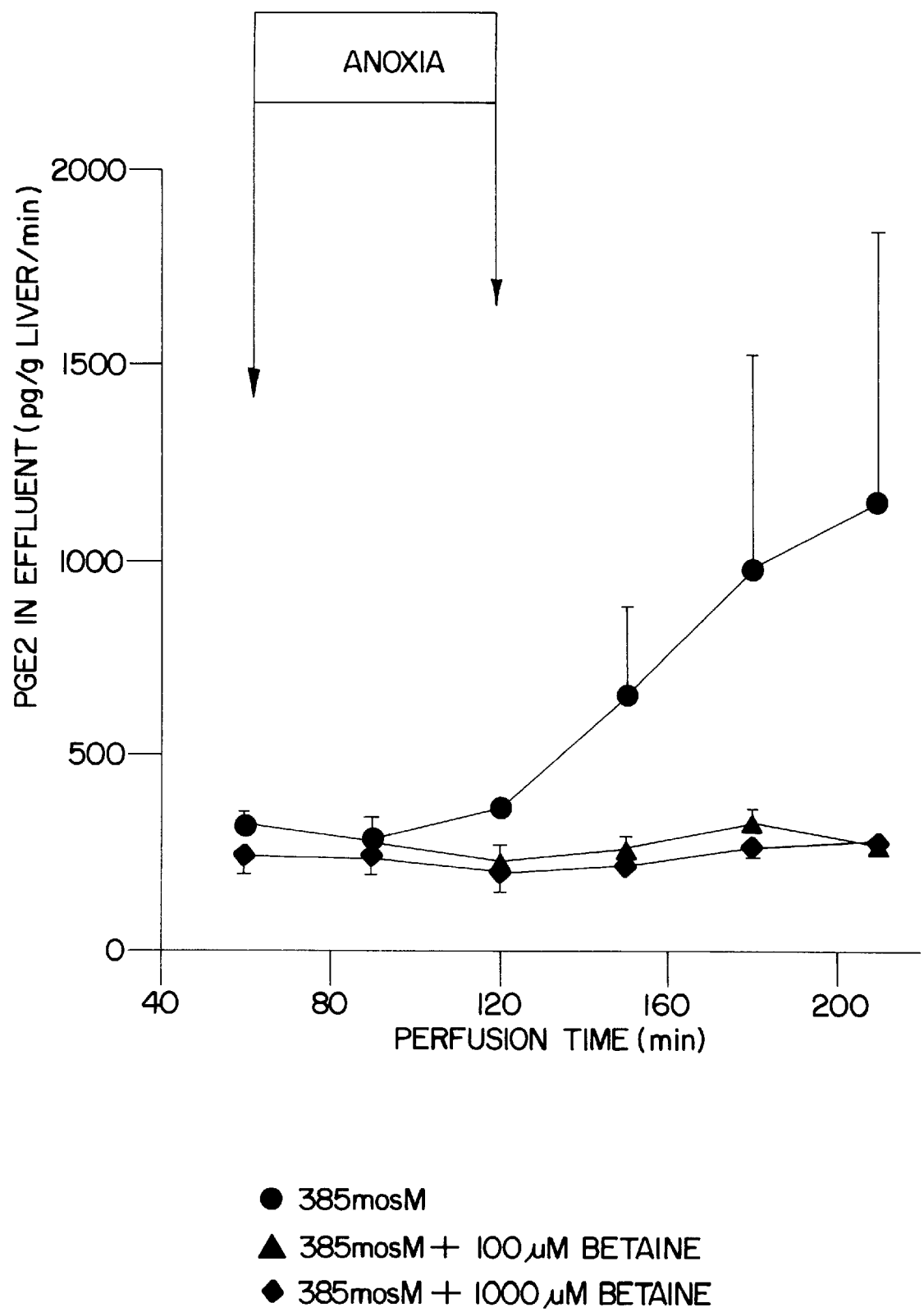
FIG. 5 shows a similar anoxic model as in FIG. 1, wherein PGE2 (prostaglandin E2) levels are measured in the effluent during anoxia and reperfusion with a 385 mosmM solution which has been provided with 0.100 mM betaine and 1 mM betaine, respectively.

It has also been demonstrated, see FIG. 5, that the decrease in LDH following betaine treatment of the liver is accompanied by a reduced liver production of eicosanoids, as represented in this experiment by the cyclooxygenase product prostaglandin E2 (PGE2). This indicates a general capacity of selected osmolytes to suppress the activity of cells capable of prostaglandin synthesis, such as macrophages and lymphocytes. The activation of immune competent cells, evident for example following ischemia/reperfusion is a major contributor to the escalating cell injury and necrosis in a process which can extend to days and months after the ischemic or hypoxic event. Accordingly, the downregulation of stimulated immune cells, achieved according to the parallel Swedish patent application, provides further support for a protective effect of selected osmolytes in the above described course of pathological events. A supplementation of osmolytes will consequently suppress the macrophage activity which can be triggered by an ischemic or hypoxic event which otherwise could lead to a rupture of vascular plaques leading to thrombosis and an even more serious organ or tissues damages resulting from occlusions of vessel lumens, see e.g. The Lancet, 1996, Vol. 347, pag. 305–306, P Weisberg et al.

FIGS. 7A and 7B demonstrates the capacity of osmolytes in protection of apoptosis, whereas FIG. 8 shows that osmolytes are effective in downregulating inducible nitric oxide synthase (iNOS). As INOS is a mediator of complications following ischemia, hypoxia and oxidative stress, these results support the utility of osmolytes in the treatment of reducing complications resulting from said stress situations.

Furthermore, a supplementation of selected osmolytes, according to the present invention, to patients identified as being at risk of acquiring life-threatening coronary syndromes of unstable angina and myocardial infarction, precipitated by the rupture of cardiovascular plaques will be of benefit, since such a therapy will selectively modulate the activity of macrophages on the plaques. The inventive osmolyte therapy, thus demonstrates a considerable potential for supplying to such at risk patients who expect complementary surgery or therapy.

This concludes that the present invention has contributing potential, in terms of treating, but also in preventing damages resulting from ischemia and subsequent reperfusion by a capacity in stabilizing vascular plaques.

A further aspect of preventing life threatening coronary syndromes by the inventive osmolyte therapy concerns patients suffering from pathologically raised levels of circulating metabolites capable of exerting osmotic stress on the vasculature, exemplified by raised levels of circulating glucose in the diabetic state. As demonstrated in the experiments shown in FIG. 2 endothelial cells subjected to osmotic stress express osmolyte transporting proteins and thereby susceptibility to osmolyte therapy for their normalization of their cellular hydration and function. Hence, osmolytes have a potential in preventing vascular dysfunctions leading to impairments of the blood flow, vascular dysfunction and related diseases in the diabetic patient, for example by being administered in connection with conventional insulin therapy as a preventive therapy for cardiovascular or other vascular diseases in the diabetic state.

Figure 6:
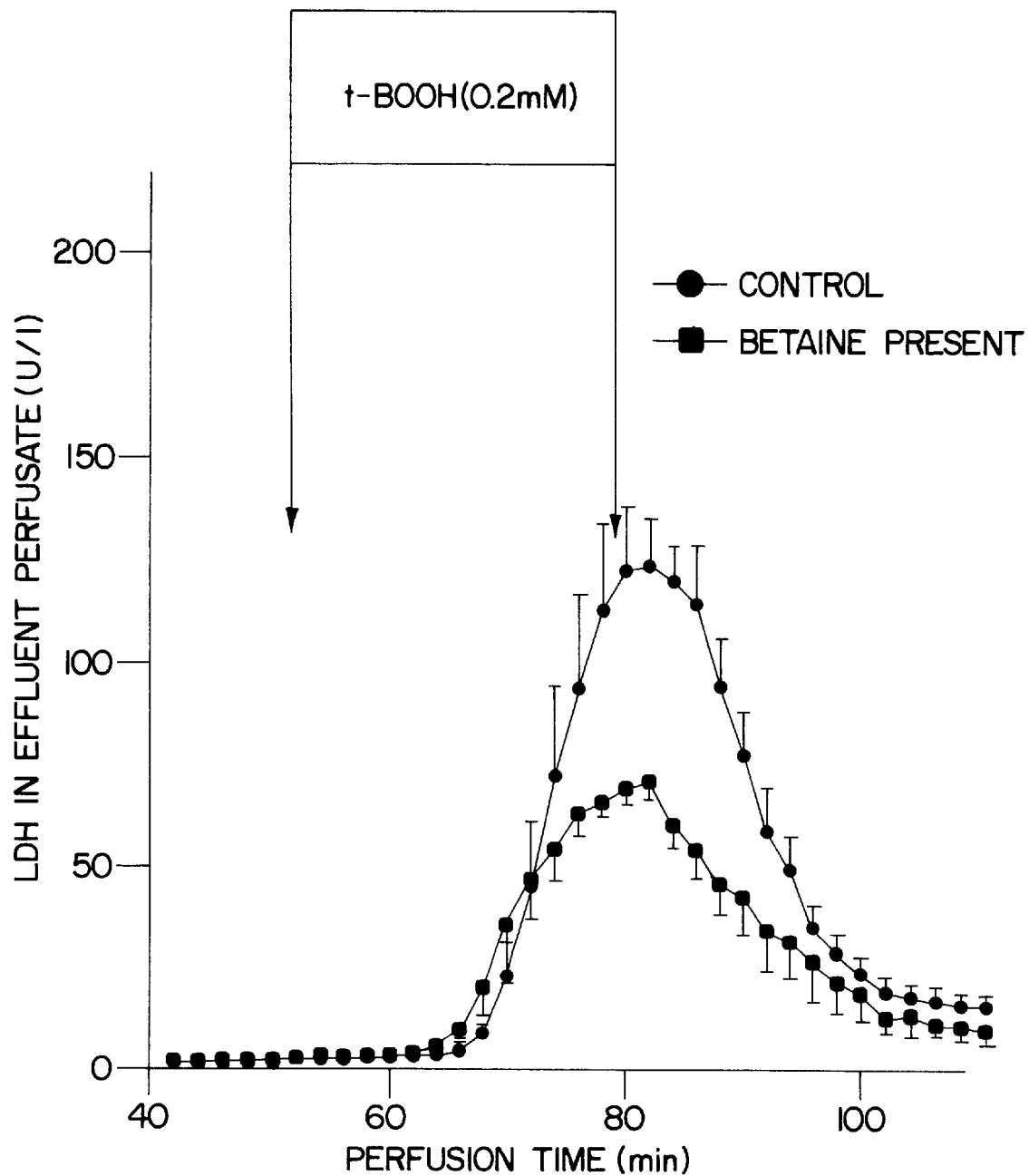
FIG. 6 shows a model for inducing oxidative stress, wherein a rat liver is exposed to a solution of 0.2 mM t-butylhydroperoxide (t-BOOH) and perfusion with a 305 mosmM solution without and with 1 mM betaine. The protective effect of 1 mM betaine in the perfusate is determined as LDH release in the effluent.

The beneficial effect of osmolytes on the tissue capacity for scavenging oxygen free radicals serves as a mechanistic basis for the described improvement of tolerance to oxidative stress as shown in FIG. 6. The extent of damages from oxidative stress, also resulting from reperfusion, can consequently be reduced therapy of supplying selected osmolytes.

I claim:

1. A method of treating or preventing complications resulting from ischemia, hypoxia or oxidative stress by affecting cells which produce mediators of said complications selected from the group consisting of immune competent cells, endothelial cells and hepatocytes with at least one organic osmolyte selected from the group consisting of polyols, amino acids and methyl amines which normally are used by said cells to regulate their hydration wherein said method comprises supplementation of an effective amount of said osmolyte to a patient suffering from one of said complications.

2. The method of claim 1 wherein said cells are protected to maintain their regular function or affected to modulate their response to the mentioned complications, for maintaining the function of vital organs challenged by pathologic events.

3. The method of claim 1, wherein said complications involve cell death.

4. The method of claim 1, wherein said complications involve an increase in the activity of inducible nitric oxide synthase (iNOS).

5. The method of claim 1 wherein said osmolyte is selected from the group consisting of taurine, betaine, inositols, and salts thereof.

6. The method of claim 5 wherein said osmolyte is selected from the group consisting of taurine, betaine, and salts thereof.

7. The method of claim 5 wherein said cells are protected to maintain their regular function or affected to modulate their response to the mentioned complications, for maintaining the function of vital organs challenged by pathologic events.

8. The method of claim 5 which further comprises administering a substance with thrombolytic capacity.

9. The method of claim 1 which further comprises administering at least one constituent capable of contributing to a prevention of the effects resulting from the ischemic or hypoxic conditions.

10. The method of claim 9, which further comprises administering a substance with thrombolytic capacity.

11. The method of claim 10 wherein said agent is capable of treating complications resulting from myocardial infarction.

12. The method of claim 1 wherein the liver, the heart or the brain is treated.

13. The method of claim 1 wherein said osmolyte comprises betaine or salt thereof.

* * * * *